US010667920B2

(12) United States Patent
Sedel

(10) Patent No.: US 10,667,920 B2
(45) Date of Patent: Jun. 2, 2020

(54) TOTAL KNEE PROSTHESIS WITH CERAMIC-ON-CERAMIC FRICTION TORQUE AND MOBILE CERAMIC PLATE

(71) Applicant: Assistance Publique—Hopitaux De Paris, Paris (FR)

(72) Inventor: Laurent Sedel, Jouy en Josas (FR)

(73) Assignee: ASSISTANCE PUBLIQUE—HOPITAUX DE PARIS, Paris (FR)

( * ) Notice: Subject to any disclaimer, the term of this patent is extended or adjusted under 35 U.S.C. 154(b) by 0 days.

(21) Appl. No.: 15/549,305

(22) PCT Filed: Feb. 5, 2016

(86) PCT No.: PCT/EP2016/052486
§ 371 (c)(1),
(2) Date: Aug. 7, 2017

(87) PCT Pub. No.: WO2016/124731
PCT Pub. Date: Aug. 11, 2016

(65) Prior Publication Data
US 2018/0036130 A1 Feb. 8, 2018

(30) Foreign Application Priority Data
Feb. 5, 2015 (FR) ...................................... 15 50908

(51) Int. Cl.
*A61F 2/38* (2006.01)
(52) U.S. Cl.
CPC .......... *A61F 2/3868* (2013.01); *A61F 2/3859* (2013.01); *A61F 2/3886* (2013.01);
(Continued)
(58) Field of Classification Search
CPC .................................................. A61F 2/3868
(Continued)

(56) References Cited

U.S. PATENT DOCUMENTS 4,888,021 A * 12/1989 Forte ....................... A61F 2/385
623/20.19
5,064,437 A * 11/1991 Stock ..................... A61F 2/3868
623/20.29
(Continued)

FOREIGN PATENT DOCUMENTS

AU 2011377371 B2 2/2017
CN 1440262 A 9/2003
(Continued)

OTHER PUBLICATIONS

International Search Report dated Feb. 29, 2016 for corresponding International Application No. PCT/EP2016/052486, filed Feb. 5, 2016.
(Continued)

*Primary Examiner* — David H Willse
*Assistant Examiner* — Javier G Blanco
(74) *Attorney, Agent, or Firm* — David D. Brush; Westman, Champlin & Koehler, P.A.

(57) ABSTRACT

A total knee prosthesis to be implanted in a human patient includes a femoral element having a longitudinal axis, a tibial plateau having a longitudinal axis and a mobile plate. The mobile plate is interposed between the femoral element and the tibial plateau to form two joints with them wherein: a) the surfaces of mutual friction of the femoral element with the mobile plate and the surfaces of mutual friction of the tibial plateau with the mobile plate are entirely constituted by one and the same massive ceramic material; and b) the mobile plate includes two condylar bowls, and the femoral element includes two condyles, the condyles and the condylar bowls each having surfaces of mutual friction spaced apart from each other by a distance smaller than 100 μm when the longitudinal axes of the femoral element and the tibial plateau form an angle of 0° to 75°.

10 Claims, 4 Drawing Sheets

(52) U.S. Cl.
CPC ............... *A61F 2310/00179* (2013.01); *A61F 2310/00203* (2013.01); *A61F 2310/00239* (2013.01)

(58) Field of Classification Search
USPC ............................................ 623/20.29, 20.33
See application file for complete search history.

(56) References Cited

U.S. PATENT DOCUMENTS

| | | | |
|---|---|---|---|
| 5,935,173 A * | 8/1999 | Roger | A61F 2/3868 623/20.31 |
| 6,554,866 B1 * | 4/2003 | Aicher | A61F 2/3868 623/20.28 |
| 7,601,176 B2 | 10/2009 | Soffiati et al. | |
| 8,540,776 B2 | 9/2013 | Bercovy et al. | |
| 2001/0018615 A1 * | 8/2001 | Biegun | A61F 2/3868 623/20.35 |
| 2006/0052875 A1 * | 3/2006 | Bernero | A61F 2/38 623/20.33 |
| 2011/0040387 A1 * | 2/2011 | Ries | A61F 2/3868 623/20.27 |
| 2011/0125278 A1 * | 5/2011 | Bercovy | A61F 2/3868 623/20.21 |
| 2012/0136452 A1 * | 5/2012 | Richter | A61F 2/3886 623/20.28 |

FOREIGN PATENT DOCUMENTS

| | | |
|---|---|---|
| CN | 101548915 A | 10/2009 |
| CN | 102112070 A | 6/2011 |
| CN | 103841923 A | 6/2014 |
| GB | 2341803 A | 3/2000 |
| WO | 2009029207 A1 | 3/2009 |
| WO | 2010001010 A1 | 1/2010 |
| WO | 2011003621 A2 | 1/2011 |

OTHER PUBLICATIONS

English translation of the International Written Opinion dated Apr. 4, 2016 for corresponding International Application No. PCT/EP2016/052486, filed Feb. 5, 2016.
English translation of the Chinese Office Action dated Sep. 4, 2018, for corresponding Chinese Application No. 201680018939.8.
Chinese Search Report dated Aug. 28, 2018 for corresponding Chinese Application No. 201680018939.8.

* cited by examiner

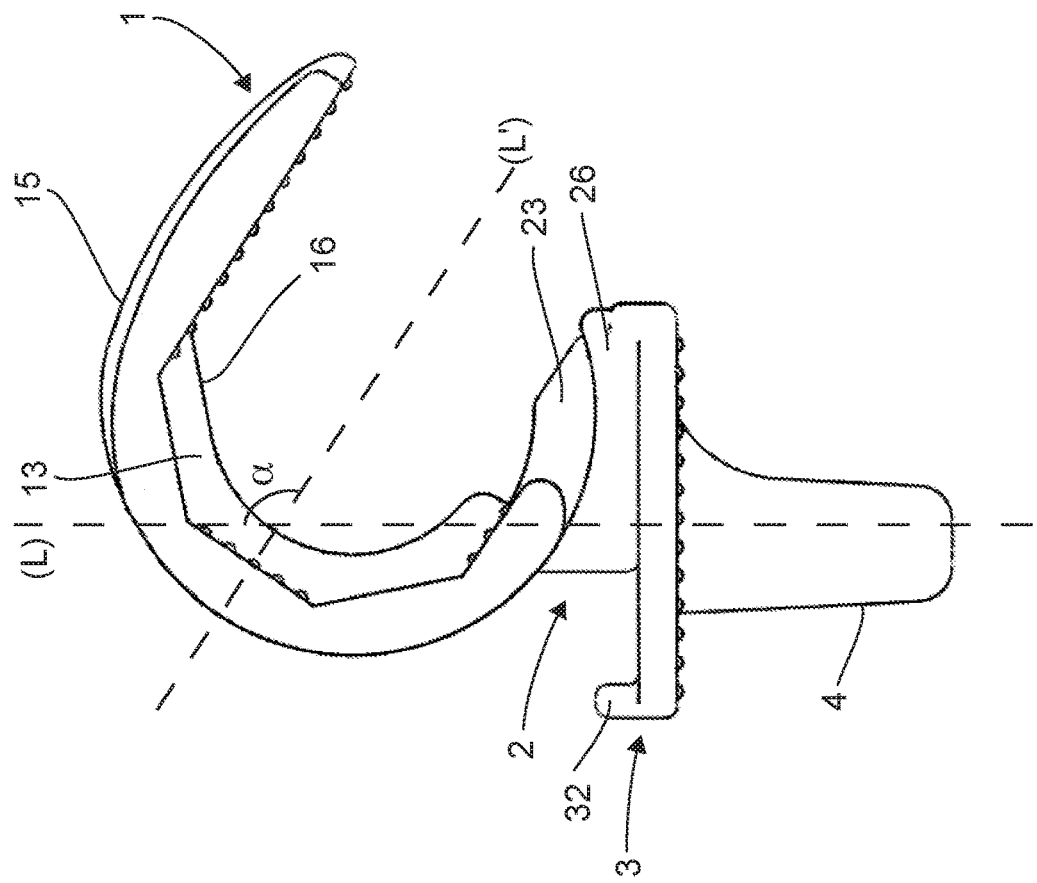
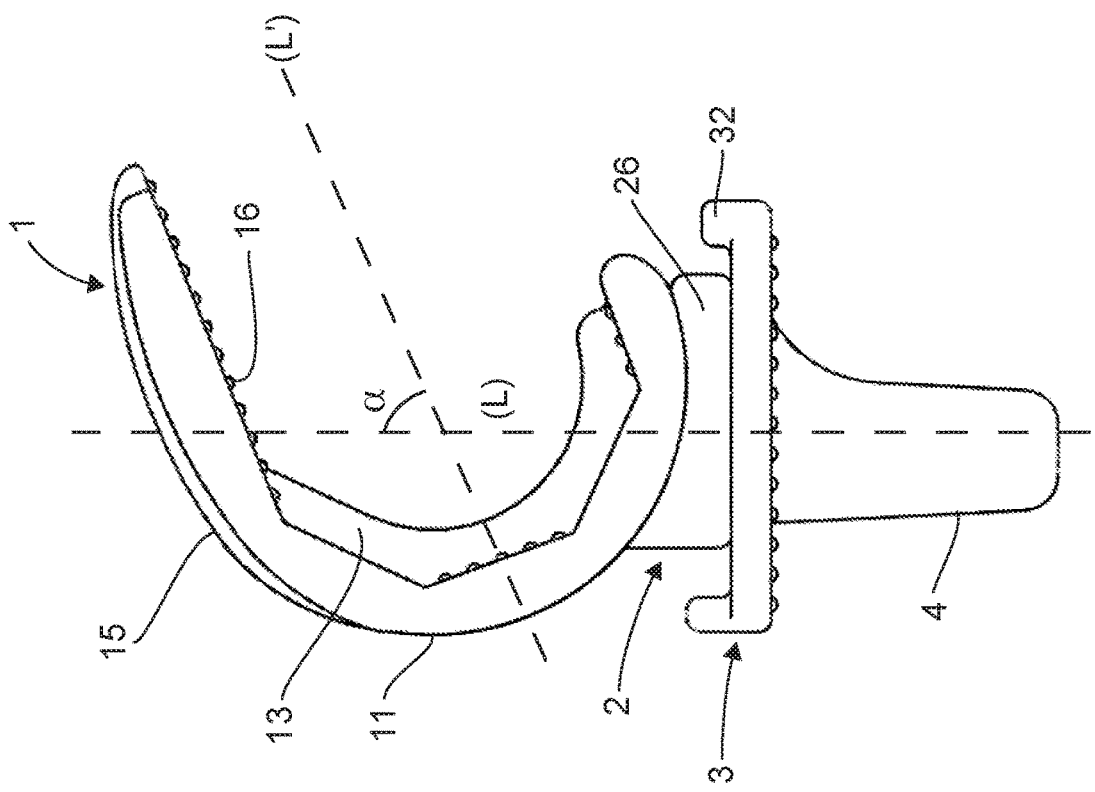

United States Patent US 10,667,920 B2

TOTAL KNEE PROSTHESIS WITH CERAMIC-ON-CERAMIC FRICTION TORQUE AND MOBILE CERAMIC PLATE

1. CROSS-REFERENCE TO RELATED APPLICATIONS

This Application is a Section 371 National Stage Application of International Application No. PCT/EP2016/052486, filed Feb. 5, 2016, the content of which is incorporated herein by reference in its entirety, and published as WO 2016/124731 on Aug. 11, 2016, not in English.

2. FIELD OF THE INVENTION

The field of the invention is that of joint prosthesis.

More specifically, the invention relates to a total knee prosthesis made of ceramic, comprising a mobile ceramic plate to replace a patient's knee joint.

3. PRIOR ART

Knee joint replacement is a frequent surgical procedure. It is estimated that, in 2011, about 650,000 prostheses were implanted in the United States and 80,000 in France. Knee prostheses can be total or partial: unicondylar, total and then hinged knee prostheses or sled knee prostheses.

Sliding (or sled) prostheses comprise a femoral condylar element and a tibial baseplate, respectively attached to the profiled extremities of the femur and tibia. The majority of prostheses implanted are what are called "sliding" prostheses. These sliding prostheses comprise a femoral part made of metal or ceramic and a tibial part made of polyethylene, generally embedded in the tibial baseplate made of metal. Certain of these prostheses have a mobile plate made of polyethylene which can move on the tibial plateau. The theoretical advantage of the mobile plate that it reduces wear on the polyethylene by enabling more consistent adaptation of the friction surfaces and improving knee flexion when the mobile plate is moved not only rotationally but also from front to rear ("drawer" movement), the mobile plate moving on the tibial surface like a meniscus.

These sliding prostheses do not replace the cruciate ligaments of the knee and must be implanted perfectly in keeping with the natural architecture of the surfaces of the knee and of the anatomical axis. Certain prostheses keep the posterior cruciate ligament while others do not. There is then a central cap that prevents the tibia from falling rearwards.

Until now, total prostheses have been made of metal and polyethylene. According to this technique, the femoral and tibial baseplates are made out of a metallic material while a polyethylene pad is mounted fixedly or movably on the tibial baseplate. Other embodiments consist of a femoral base made of ceramic cooperating with a polyethylene plate, mounted on a tibial baseplate made of ceramic or metal. When the prosthesis is designed with a mobile plate, the mobility of the mobile plate can be limited by the shape of the metal receptacle fixed into the tibia which permits only rotational movements or it can be limited by a central nipple which, depending on the shape of a lower cavity designed in the mobile plate, permits rotational and drawer movements.

However, these materials cannot be used to design a joint prosthesis that is robust enough to allow the patient to resume normal physical activity: while a knee prosthesis makes it easy to resume painless walking, patients generally feel some discomfort during prolonged walking or when walking up or down stairs. Besides, running or any other major physical activity remains prohibited.

Now, the average age of patients is dropping considerably. Many surgical operations indeed are a consequence of sports-related or work-related accidents among young and professionally active people. It is therefore difficult and particularly frustrating for people to have to give up any form of physical activity or even their professional activity.

In addition, the failure rate of these prostheses is currently 10% at the end of the first 10 years. The rate rises to 25% among younger patients. The failure of the prosthesis means that another operation has to be performed on the patient in order to replace his prosthesis. Now these repeat surgical operations entail, on the one hand, a great deal of suffering for the patient and, on the other hand, a considerable cost for health insurance systems. They also represent a legal risk for nursing homes and hospitals.

However, the main cause of these failures lies chiefly in the in the wearing out of the polyethylene constituting friction torque. The release, under mechanical stresses, of wear particles causes an inflammatory reaction that is responsible for joint effusion as well as the creation of a granuloma of periarticular resorption. Bone lysis in those parts of the femur and/or the tibia that neighbor the prosthesis has been observed, possibly resulting in major bone loss. This osteolysis can also lead to the loosening of the prosthesis. When the wear is very great, the metal parts can be bared, leading to reactions of massive rejection through the production of toxic metal particles (metallosis).

There is the known document WO-2011/003621-A1 which especially describes partially ceramic knee prosthesiss as well as a wear resistant device for these prostheses. However, no prosthesis according to this technique has appeared to date on the market. This is the case for the following reasons.

First of all, the prostheses according to this document comprise a metal rod to which a tibial baseplate is fixed. This leads to high abrasion of the metal. The abrasion of the metal results in the formation of metal debris in the body. The organism reacts against these metal particles by producing an inflammatory reaction like that described with polyethylene particles.

In addition, affixing the ceramic parts to a metal rod raises problems: it is in practice very difficult to affix this type of element without creating conditions of breakage of the ceramic. Besides, the document WO 2011/003621 A1 describes no method for affixing these parts. In addition, although the mobile plate described is made of ceramic, the wide oval aperture at the center of the mobile plate is in practice impossible to make in a material using massive ceramic since this shape of aperture and its dimensions make the ceramic brittle. Similarly, the impact of the aperture made in the ceramic plate against the stops 18 is such as to induce premature fractures of the ceramic plate, if this plate were to be made of massive ceramic.

One solution for countering these drawbacks is to propose ceramic-coated metal parts. However, the fine layer of ceramic on the surface of the metal gets worn out and the metal can be bared, prompting the inflammatory reactions referred to here above. This practice has not for the time being shown any sort of superiority.

It is therefore necessary to design total knee prostheses that are more wear resistant, so that the wear particles produced do not cause inflammatory reactions, thus enabling the patients to return to normal life. It is also desirable that the prosthesis or its debris should produce a dense fibrous tissue capable to stabilizing the knee in a way that ligaments would do.

4. SUMMARY OF THE INVENTION

These goals as well as others that shall appear here above are achieved by means of a total knee prosthesis intended for being implanted in a human patient, said prosthesis comprising a femoral element having a longitudinal axis, a tibial plateau having a longitudinal axis and a mobile plate, said mobile plate being interposed between the femoral element and the tibial plateau to form two joints with them wherein:
  a. the surfaces of mutual friction of the femoral element with the mobile plate and the surfaces of mutual friction of the tibial plateau with the mobile plate are entirely constituted by one and the same massive ceramic material; and
  b. the mobile plate comprises two condylar bowls, and the femoral element comprises two condyles, said condyles and said condylar bowls each comprising surfaces of mutual friction spaced apart from each other by a distance of less than 100 μm when the longitudinal axes of said femoral element and said tibial plateau form an angle of 0° to 75°.

This distance enables perfect congruency between the surfaces of mutual friction especially in a load-bearing area (for example in a static standing position or in movement).

In the following description of the invention, the longitudinal axis of the femoral element essentially coincides with the axis of the femur of the patient in whom the prosthesis will be implanted. Similarly, the longitudinal axis of the tibial plateau essentially coincides with the longitudinal axis of the tibia of the patient receiving the prosthesis. The term "essentially coincides with" is understood to mean that the two reference axes form an angle of less than 5° with each other, alternatively less than 2°, and alternatively again less than 1°, and alternatively again an angle equal to 0°.

Thus, the prosthesis according to the invention comprises three ceramic elements made of massive alumina ceramic intended for being hinged relatively to one another, along two joints with congruent surfaces. The femoral element fits into the prepared distal extremity of the femur and reproduces the shape of the trochlea. It is therefore necessary to have a right femur element and a left femur element. The tibial plateau is anchored in the upper extremity of the tibia that is prepared to receive it. Finally, the mobile plate is situated between the femoral element and the tibial plateau to form a joint. The invention therefore relies on a wholly novel and original approach to designing a total bicondylar knee prosthesis in which all the surfaces in contact with the elements that form it are made out of a same ceramic material. This favors a reduction in the quantity of wear debris inasmuch as the designing of the parts with two distinct joints makes it possible to preserve close contact, in all degrees of flexion of the knee, between the surfaces, this being a major factor for reducing the quantity of debris formed. This contact or congruency is obtained both in the load-bearing area and in the flexion area.

Unlike in current prostheses which comprise a femoral element made of metal or ceramic, in contact with a fixed or mobile plate made of polyethylene, the prosthesis according to the invention comprises a mobile plate made of a massive ceramic material that is the same as that of the femoral element.

According to the invention, the femoral element, the mobile plate and the tibial plateau are entirely constituted out of one and the same ceramic material. In other words, the femoral element, the mobile plate and the tibial plateau are all three made of massive ceramic, which means that they do not include any alloy with plastic material or metal material such as polyethylene, titanium, metalized ceramic etc., or that they are not constituted by a fine layer of ceramic fixed to a metal or plastic element.

Until now, to the knowledge of the present Applicant, it has never been proposed to place two ceramic parts in close contact to design a knee prosthesis. There have been known ways of proposing ceramic hip prostheses among young and/or active individuals. However, the mechanical stresses exerted on the knee joint are very different from those exerted on the hip, since the hip and knee joints have very different geometries. The use of ceramic to make a knee prosthesis in which the friction surfaces of the tibial plateau and the femoral element are made entirely out of ceramic has always been rejected by prosthetic specialists and orthopedic surgeons, for various reasons. The first reason is that the mechanics of the knee is complicated. During flexion, there are successive phases of rolling and sliding. These phases are tolerated by a pair of materials constituted by hard/soft materials but cannot be envisaged with a pair of hard/hard materials, since this latter pair does not work satisfactorily at the tribological level unless high congruency persists between the friction surfaces.

The second reason is that ceramics is a material with brittle behavior and can break in the propagation of a crack. Apart from the health risk for a patient, cases of breakage of prosthesis entail costs and major legal risks for health professionals. This must be compared with the tenfold risk of repeat surgery due to the consequences of reactions to wear debris in prostheses containing polyethylene.

Another prejudice against the use of ceramic in total knee prosthesis comes from the possibility that mutual friction between the two ceramic parts will produce a scratching sound at each movement, this sound being heard by the patient and sometimes even by people surrounding him. This phenomenon has already been observed in certain hip prostheses and can be a source of discomfort in daily life for the patient. The designing of parts as well as the interposing of metal particles is the factor most frequently implicated in this problem. The invention prevents this drawback by providing for a sufficient thickness of ceramic and by eliminating the ceramic/plastic or ceramic/metal surfaces of mutual friction. Besides, the parts of the prosthesis according to the invention can be fixed into the bone with an acrylic cement that dampens vibrations.

Preferably, said ceramic material has a thickness of 4 mm to 14 mm. The Applicant has indeed noted that ceramic prostheses having thicknesses outside this range, are brittle. This is not desirable. In particular, prosthetic prototypes have been proposed wherein a fine layer of ceramic is attached to the metal part. Such prostheses are extremely brittle and are therefore not used in the form of ceramic/ceramic friction elements.

Another advantage of ceramic is that it is better tolerated by the organism than metal or polyethylene. The advantage of ceramic-on-ceramic friction is that it enables the recreation of fibrous tissue or a "neo-ligament" acting as a natural ligament after adaptive remodeling. Indeed the formation of a fibrous tissue is observed. This fibrous tissue is more resistant and of better quality with the prostheses according to the invention than it is with the usual prostheses in which the friction surfaces are constituted by metal against polyethylene or ceramic against polyethylene. The wear particles generated in small quantities during the movements of the joint do not give rise to macrophage reaction in the organism. The prostheses of the invention therefore avert the problem of osteolysis and the risks of dislocation of the prosthesis observed with present-day prostheses.

Quite to the contrary, the Applicant has observed that small quantities of alumina particles give rise to a particularly dense fibrous tissue, even denser than that formed around current prostheses. This fibrous tissue plays a role in reinforcing and stabilizing the joint capsule and replacing the ligaments. The prosthesis of the invention therefore enables patients to have a knee joint that is more stable and resistant to forces. This particular feature therefore enables patients to keep their prosthesis for a longer time and to recover normal physical activity.

The Applicant has furthermore noted that the behavior of two ceramic parts against each other gives a prosthesis that is highly resistant and more robust than existing ones, contrary to the prejudices listed here above. These special technical advantages are due especially to perfect congruency between the friction surfaces, which reduces friction between the parts and therefore the risk of wear in the prosthesis.

As understood in the invention and in the following description, the perfect congruency of the parts relative to each is obtained when the parts perfectly match each other, i.e. with very limited clearances between the surfaces in contact, and when there is no area of the surfaces of friction of the parts relative to each other in which the mechanical stresses are concentrated. This perfect congruency can also be qualified as being ideal in the description.

This perfect congruency or ideal congruency of the surfaces of mutual friction is obtained through the choice of simple shapes for the surfaces: the condylar/condylar bowl surfaces are portions of cylinders and/or spheres having the same radius of curvature and the surface of contact between the mobile plate and the tibial plateau is plane. These shapes are obtained by specific manufacturing and honing techniques, mastered by the industry specializing in ceramic prostheses. To put it briefly, the profiles of the different parts produced are evaluated by measuring the radii of curvature of the different parts after these parts are subjected to different wear tests. The goal of these measurements is to obtain a spacing between the parts and more specifically between the mobile plate and the femoral element.

According to the invention, the space between the surfaces of mutual friction of the femoral element and the mobile plate ranges from 0 µm to 100 µm, preferably from 10 µm to 60 µm, when the longitudinal axes (L, L') of said femoral element and said tibial plateau form an angle of 0° to 75° with the longitudinal axis of the mobile plate.

Advantageously, the space included between the surfaces of mutual friction of the mobile plate and the tibial plateau also ranges from 0 µm to 100 µm, preferably from 10 to 100 µm, and even more preferably from 10 µm to 60 µm.

Selecting the distance between the surfaces of mutual friction is of prime importance. Indeed, the inventors have shown surprisingly that, in order to ensure optimal congruency without impairing the comfort and the operation of the prosthetic joint, this distance should preferably not be less than 10 µm and more than 100 µm, preferably not more than 60 µm. Indeed at a distance of less than 10 µm, there is a risk that the liquid will not flow sufficiently. If is over 100 µm, there is a risk of concentration of stresses on one part of the prosthesis that will become excessively high.

For all these reasons, the prostheses according to the invention are more resistant, and limit or even prevent the drawbacks observed with present-day prostheses in which the mobile plate is made of polyethylene. The present invention thus enables patients to return to normal life with a greater level of physical activity than that allowed to them at the present time. It is no longer necessary to carry out repeat surgery to replace used prostheses or, at the very least, the date of the second operation is considerably later than with present-day prostheses.

Until now, it was considered to be impossible to design a total knee prosthesis in which the elements forming the joint—i.e. the femoral element, the mobile plate and the tibial plateau—were entirely made of massive ceramic because no adequate design was proposed for this. It was indeed not possible, with existing designs, to maintain perfect congruency during the totality of the movements, this congruency being indispensable when the ceramic must be made to be in friction with itself. The particular design of the prosthesis according to the invention around a mobile plate with a specific shape and the spacing planned between the surfaces together eliminate these areas of concentration of mechanical stresses and therefore enable the manufacture of total knee prostheses in which all the elements forming the joint are made of massive ceramic.

This is therefore a selection of particular specific characteristics that enable the designing and implementing of a total knee prosthesis made of ceramic.

Preferably, the ceramic material is an alumina ceramic ($Al_2O_3$) that brings about the synthesis of a fibrous tissue of better quality than that obtained with other ceramics. Such materials are of a quality fit for surgery i.e. they must comply with prevailing standards on materials for the manufacture of surgical prostheses. For example, alumina ceramic can be a dense polycrystalline ceramic obtained with aluminum oxide powder compressed at temperatures of about 1600° C. through the HIP (High Isostatic Pressure) method. One ceramic suited to the implementing of the invention is a ceramic that complies with the ISO-6474-1 standard.

Preferably, the ceramic has a grain size of less than 2 µm. Even more preferably, the ceramic used to manufacture the prosthesis according to the invention has a grain size of 0.5 µm to 2 µm. Even more preferably, the ceramic has a grain size of 1 µm to 2 µm. The grain size of the ceramic material is determined according to any method well known to those skilled in the art.

In one promising variant of the invention, the femoral element is also capable of cooperating with the patient's patella via a protrusion that mimics a trochlea on the anterior part of the femoral element.

Advantageously, the tibial plateau is anchored by its lower face in the upper extremity of a patient's prepared tibia. A design taking the form of a massive rod that is integral with the tibial plateau is fixed into the patient's bone by acrylic cement.

The dimensions of the parts constituting the prosthesis depend on the size and dimensions of the joint to be replaced. For example, the mobile plate can have a maximum thickness of 4 mm to 14 mm. This ceramic thickness is sufficient to ensure stability of the knee while preventing the risk of fracture of the ceramic.

Advantageously, said condylar bowls and said corresponding condyles are spaced apart from one another by a distance of less 100 µm, preferably a distance of 10 µm to 100 µm and more preferably a distance of 10 µm to 60 µm, when the longitudinal axis of the femoral element and longitudinal axis of the tibial plateau form an angle of 0° to 60°. The angular range of 0° to 60° corresponds to the load-bearing area of the prosthesis. The load-bearing area is defined by the zone and amplitude of flexion of the knee on which the joint supports the essential part of the patient's weight.

Advantageously, the femoral element and the tibial plateau are mobile in rotation relative to each other on an angular range of flexion of 0° to 135°.

In other words, the longitudinal axis of the tibial plateau and the longitudinal axis of the femoral element can form an angle of 0° to 135°.

As understood in the invention, the mobile plate is mobile in a forward/rear, lateral and/or pivoting direction about a longitudinal axis. Thus, the mobile plate of the invention is never solely rotational.

This characteristic enables the patient receiving the prosthesis to be freer in his movements and especially in his ability to climb a staircase, bend his knee to crouch or kneel or simply have more amplitude in his movements without feeling any block. The movements allowed by the knee prosthesis of the invention are then very close to the natural movements allowed by the knee. It is the movement proper to each patient's knee that creates the positioning of the areas of newly formed fibrous tissue and thus makes it possible, after a few weeks, to obtain the anticipated result. This amplitude of movement for example is not allowed by the prosthesis described in the document WO-2011/003621-A1, which cannot bend beyond 90°, thus preventing the patient from going up a staircase for example and making it impossible to propose the prostheses described in this document to a patient.

In one promising embodiment, the surfaces of mutual friction of the condyles and of the condylar bowls are cylinder portions generated by revolution and having a same radius R.

In another embodiment, the surfaces of mutual friction of the condyles and the condylar bowls are sphere portions having a same radius R'.

In another embodiment, one of the surfaces of mutual friction of the condyles and the condylar bowls is a sphere portion having a radius R' and the other one is a cylinder portion generated by revolution having a radius R, the center of the sphere being on the axis of revolution of the cylinder.

The shape of the cylinder portion and/or sphere portion can be appreciated when we look at a sagittal section of the prosthesis, made at about 20 to 27 mm from the median plane of the prosthesis according to the invention. Those skilled at the art will know how to easily determine the way to place the sagittal plane.

It must be noted that natural condyles generally have a spherical shape formed by several successive spheres, the radii of which diminish from front to rear, the center of the spheres having an elliptic shape. The Applicant herein proposes a shape that is slightly different from the natural shape, making it possible to provide ideal congruency of the elements of the prosthesis relative to each other during the movement of the knee and therefore their ceramic embodiment. Indeed, the centers of the cylinder or sphere portions of the surfaces of friction between the mobile plate and the femoral element are not on an ellipse but on an axis.

In some variants, R and R' can be equal. The dimensions of the prostheses and parts constituting them are easily determined by those skilled in the art. It is indeed common practice to propose different sizes of prostheses to adapt to different sizes of patient operated upon.

These three embodiments make it possible to design a prosthesis in which the mechanical constraints are not concentrated on a precise area, which could induce a crack in the ceramic.

Advantageously, said mobile plate comprises an intercondylar stud forming a projection towards said femoral element, said femoral element comprising an intercondylar gap or empty space that houses said intercondylar stud. Thus, the femoral element and the mobile plate cooperate along a third series of surfaces of mutual friction. Preferably, the intercondylar gap and the intercondylar stud are cylinder portions or sphere portions. If the intercondylar stud and the intercondylar gap are cylinder portions, they are coaxial with the cylinder portions forming the condyles and condylar bowls. If the intercondylar stud and intercondylar gap are sphere portions, the center of this sphere is situated:
   either on the axis of revolution of the cylinder portions forming the condyles and condylar bowls;
   or on the axis connecting the centers of the sphere portions forming the condyles and condylar bowls.

The intercondylar stud and the intercondylar gap together provide stability and at the same time center the relative movement of the femoral element and of the mobile plate. The intercondylar stud abuts the extremities of the slot, thus limiting the amplitude of the movement during extension.

The radius R" of the sphere portion or of the cylinder portion form the intercondylar gap and can range from 14 mm to 30 mm, preferably 17 mm to 25 mm.

It must be noted that the radii R, R' and R" are measured between the axis of the cylinder generated by revolution or the center of the sphere, and the surface of friction of one part against the other.

Advantageously, said gap and condylar stud are spaced apart from each other by a distance of 0 μm to 100 μm, preferably 10 μm to 100 μm, and even more preferably 10 μm to 60 μm when the longitudinal axis of the femoral element and the longitudinal axis of mobile plate form an angle of 0° to 60°.

Advantageously, R and R' have a length of 22 mm to 38 mm, preferably 25 mm to 35 mm.

The Applicant has noted that these special dimensions make it possible to design knee prostheses for individuals of differing body mass while preventing the concentration of stresses on a precise area of the ceramic material. In other words, these particular dimensions make it possible to obtain the perfect congruency needed to obtain a prosthesis according to the invention, wherein the femoral element, the mobile plate and tibial plateau are made of massive ceramic.

Advantageously, said mobile plate has a perimeter smaller than the perimeter of the upper surface of the tibial plateau. This characteristic enables the prosthesis to have a slightly pivoting movement about the longitudinal axis of the mobile plate and the tibial plateau, this longitudinal axis essentially coinciding with the longitudinal axis of the tibia. It must be noted that the longitudinal axis of the mobile plate is essentially parallel, preferably perfectly parallel, to the longitudinal axis of the tibial plateau.

In one advantageous embodiment, said tibial plateau comprises at least three stops forming a projection towards said mobile plate, said stops making it possible to limit the movements of the mobile plate on the surface of the tibial plateau.

The stops prevent uncontrolled translation of the mobile plate on the surface of the tibial plateau. The stops therefore define a perimeter of free but controlled movement of the mobile plate relative to the tibial plateau. Thus, the movements permitted by the prosthesis are very close to the movements of a natural knee.

Advantageously, the surface of mutual friction between said mobile plate and said tibial plateau is essentially plane. Preferably, the surface of mutual friction between said mobile plate and said tibial plateau is perfectly plane. Thus, the sliding and/or translational movements of the plates relative to each other are almost devoid of friction or completely devoid of friction. Lacking rough surfaces, the risks of wear are limited. The movement of the knee is therefore more fluid and more natural.

In one advantageous embodiment, said mobile plate can pivot on said tibial plateau about an axis at an angle of +/−15°. In other words, the transversal axis of the mobile plate can form an angle of 15° relative to the transversal axis on the tibial plateau. It can noted by convention that there is pivoting of +15° when the movement takes place in the clockwise sense and −15° when the movement takes place in the anticlockwise sense. This amplitude of movement is sufficient to ensure the rotational movements of the natural knee, especially during flexion of the knee.

In one advantageous embodiment, the parts forming the prosthesis according to the invention have no holes and/or perforations. Thus, the femoral element, the tibial plateau and the mobile plate have no holes or perforations. If we consider these parts to be made out of a same massive ceramic material, it follows that the integrity of the ceramic is preserved by not making any hole or any perforation therein. This further contributes to the resistance of the prosthesis.

In one advantageous embodiment, each part forming the prosthesis is a unit part. Thus, the femoral element, the tibial plateau and the mobile plate are each formed by a unique part made out of a massive ceramic material. On the contrary, none of these parts comprises an additional secondary part. Similarly, none of them is formed by an assembly of at least two distinct parts. This further contributes to the resistance of the prosthesis and to the simplicity of design.

5. LIST OF FIGURES

Other features and characteristic of the invention shall appear more clearly from the following description of a preferred embodiment, given by way of a simple illustrative and non-exhaustive example and from the appended drawings of which:

FIG. 3 is a sagittal section of the prosthesis according to the invention when the longitudinal axis of the femoral element and the longitudinal axis of the mobile plate form an angle of 45°;

FIG. 4 is a sagittal section of the prosthesis according to the invention when the longitudinal axis of the femoral element and longitudinal axis of the mobile plate form an angle of 135°;

6. DESCRIPTION OF ONE EMBODIMENT OF THE INVENTION

The general principle of the invention relies on a total prosthesis for a knee in which the mobile plate, the femoral element and tibial plateau have surfaces of mutual friction made out of one and the same ceramic material. These surfaces of mutual friction are perfectly congruent because of the optimizing of the shape of the surfaces of mutual friction and of the respective distance between the parts. Contrary to the hitherto common and widespread view, ceramic can be used to obtain a particularly resistant knee prosthesis.

This resistance is especially due to the perfect congruency of the parts relative to each other and especially of the mobile plate relative to the femoral element and the mobile plate relative to the tibial plateau. The perfect congruency of the mobile plate with the femoral element provides for optimum friction while generating a minimum of wear debris; its mobility reproduces the overall play of the joint. This play can be sub-divided into two movements: that of the femoral element on the mobile plate associated with the rotational mobility and a drawer-like movement of the mobile plate on the surface of the tibial baseplate. The entire innovation therefore prevents or at least restricts the probabilities of repeat surgery on the knee, especially for young and physical active patients. It furthermore improves the results of the knee prosthesis in terms of the comfort and stability. This perfect congruency is obtained through studies on the part of the inventors, leading to the development of surfaces of mutual friction that prevent the creation of a concentration of mechanical stresses in the prosthesis. The congruency therefore prevents the phenomenon of abnormal wear of the ceramic material.

Figure 1:
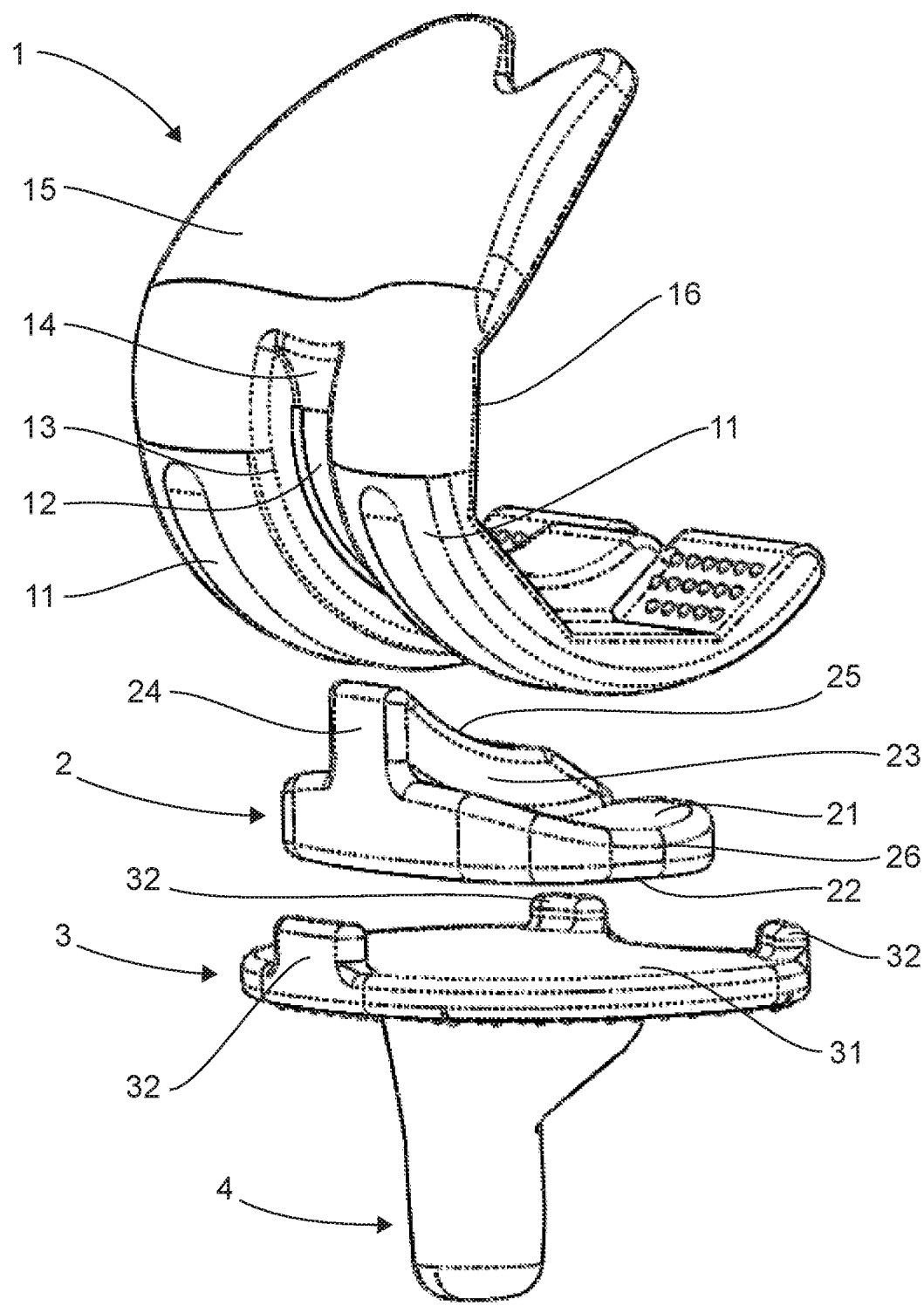
FIG. 1 is a perspective or three-quarter, exploded view of the prosthesis according to the invention.

Referring to FIG. 1, we present a three-quarter and exploded view of the prosthesis according to the present invention.

As can be seen in FIG. 1, the prosthesis according to the invention comprises a femoral element 1, a mobile plate 2 and a tibial plateau 3 fixed to an anchoring heel 4 that is to be mounted on a upper profiled end of a tibia.

The femoral element 1 has the general shape of a hollow partial shell externally defining two condyles 11 appreciably reproducing the shape of natural condyles, the posterior floating part of which, however, with the mobile plateau are cylinder portions and not irregular sphere portions. The condyles 11 could also be sphere portions. The condyles 11 are separated by a slot that on the whole reproduces the natural intercondylar gap 12. The intercondylar gap 12 has two appreciably parallel lateral surfaces 13. The intercondylar gap 12 corresponds to a cylinder portion coaxial with the cylinder portions forming the condyles 11 but with a smaller radius. The intercondylar gap 12 can also take the form of a sphere portion, the center of which is on the axis of revolution of the cylinder portions forming the condyles 11 or on the axis connecting the center of these spheres when the condyles are sphere portions.

Internally, the femoral element defines a femoral housing 16 that is to receive the profiled lower extremity F1 of a femur F. The femoral element 1 can have a protrusion on its anterior face 15 that mimics the trochlea and is intended to cooperate with the patient's patella.

The mobile plate 2 is inserted between the femoral element 1 and the tibial plateau 3. The mobile plate has a lower surface 23 that is essentially or even perfectly plane. On its upper surface, the mobile plate 2 has two condylar bowls 21 separated by an intercondylar stud 24. The intercondylar stud has a surface 25, the shape of which corresponds to the gap 12 as well as two lateral surfaces 23, the shape of which corresponds to the lateral surfaces 13 of the gap. A slight interstice enables the natural liquids to lubricate the joint formed by the prosthesis.

The condylar bowls 21 define areas or surfaces of mutual friction, respectively for the two condyles 11 of the femoral element 1. Advantageously, the bowls 31 and the condyles 11 have surfaces of mutual friction of a perfectly congruent cylindrical shape. This significantly reduces the friction and therefore the wear on these parts. The term "perfectly congruent" will be understood to mean that the parts fit in perfectly with each other and that they are spaced apart at a distance of about 0 µm to 100 µm, preferably from 10 µm to 100 µm and even more preferably from 10 µm and 60 µm, especially when the angle between the longitudinal axis of the femoral element and of the mobile plate forms an angle of 0° to 75°.

As for the intercondylar stud 24, it is engaged in the intercondylar gap 12 of the femoral element 1. The femoral element 1 abuts the surface 14 in the intercondylar gap 12 so that the relative movement of the mobile plate 2 and of the femoral element 1 remains controlled in its amplitude.

During the rotation of the femoral element 1 on the mobile plate 2, the condyles 11 slip or slide in the condylar bowls 21 with the intercondylar stud 32 which moves in the intercondylar gap 12 that forms a sort of rail.

The mobile plate 2 can move freely in translation without any stress on the tibial plateau 3, the lower surface 22 of the mobile plate and upper surface 31 of the tibial plateau being both essentially or even perfectly plane.

The tibial plateau has an upper surface 31 that is to cooperate with the lower surface 22 of the mobile plate 2. The mobile plate 3 has three stops 32 on its upper surface. These three stops 32 restrict the translational motion of the mobile plate 2. On its lower face, it has a massive rod made of alumina ceramic that is to be cemented in the upper extremity of a patient's prepared tibia.

Indeed, the mobile plate 2 herein fulfils the role of the meniscus. Its perimeter is smaller than that of the tibial plateau 3 so that it can enter into movement within the limits of the space defined by the stops 32. It can therefore slide in translation from front to rear and/or laterally on the upper surface of the tibial plateau: this has the effect of allowing further degrees of freedom in movement for the patient and a movement very close to the natural movement of the knee. It can also pivot about its longitudinal axis, parallel to the axis of the tibial plateau.

The femoral element 1, the mobile plate 2 and the tibial plateau 3 are all three made out of ceramic $Al_2O_3$ according to the ISO-6474-1 standard.

Figure 2:
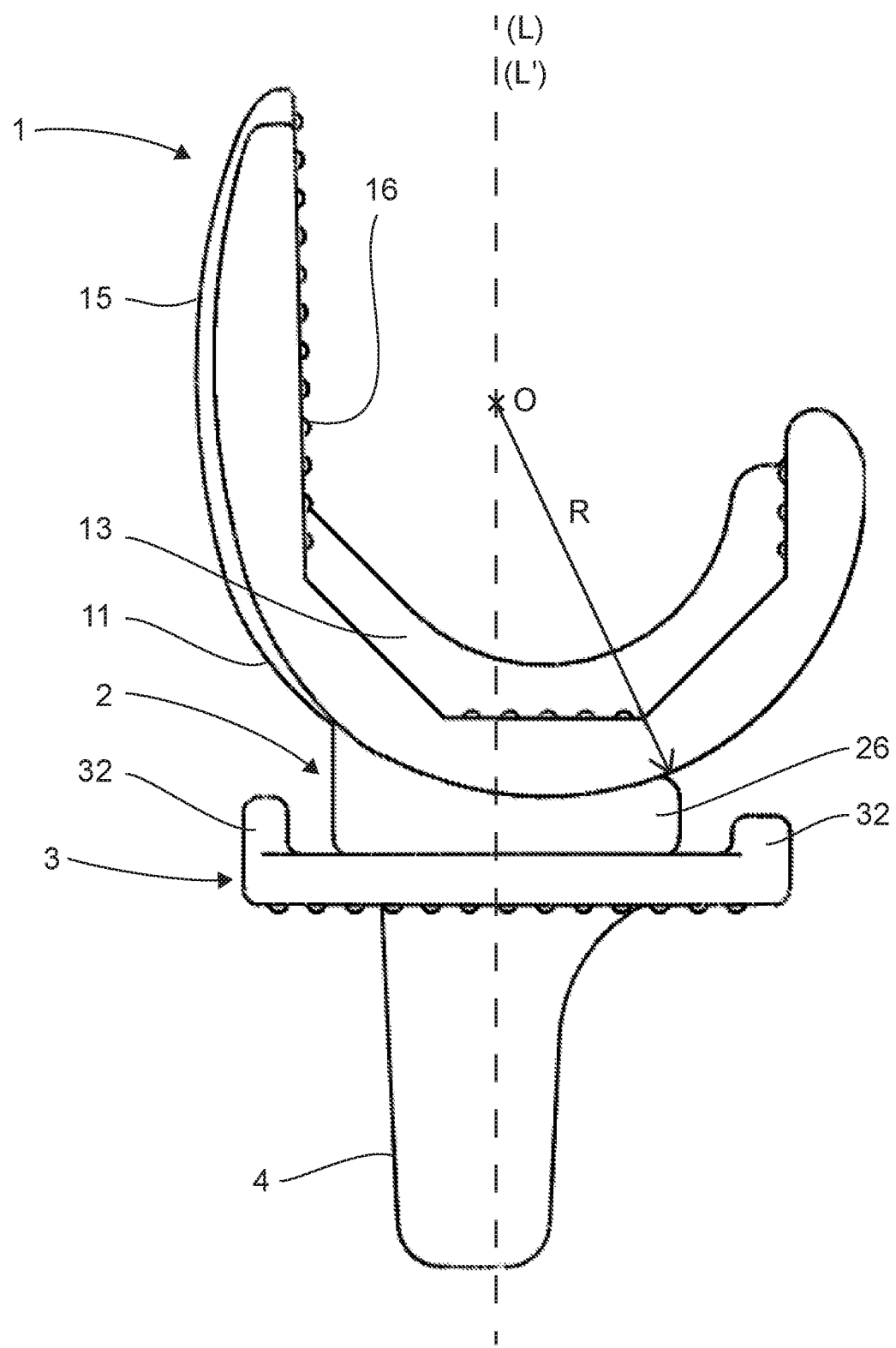
FIG. 2 is a sagittal section of the prosthesis according to the invention when the longitudinal axis of the femoral element and the longitudinal axis of the mobile plate form a zero (0°) angle.

FIGS. 2, 3 and 4 are sagittal sections of the prosthesis assembled according to the invention. The references are identical with those of FIG. 1. These sections are made in a sagittal plane spaced apart by a distance of about 20-27 mm from the median plane of the prosthesis.

As can be seen in FIG. 2, the longitudinal axis L of the tibial plateau and the longitudinal axis L' of the femoral plate herein form a zero (0°) angle. In FIG. 3, the axis L and L' form an angle α of about 45°. This corresponds approximately to the angle formed by the knee when walking. In FIG. 4, the angle α formed by the angles L and L' is about 135°. This enables the patient to walk up staircases or perform moderate exercise.

As can also be seen in FIG. 2, the condyles 11 are formed by cylinder portions with a radius R, the axis of revolution of which intersects the axis L and L' at the center O. It must be noted that the condyles could be sphere portions with a center O and a radius R'. Preferably, the radii R and R' have a length of 22 mm to 38 mm, preferably 25 mm to 35 mm. The radius R" of the intercondylar gap cannot be shown in these sections. The surface of the gap is herein concealed.

Figure 5A:
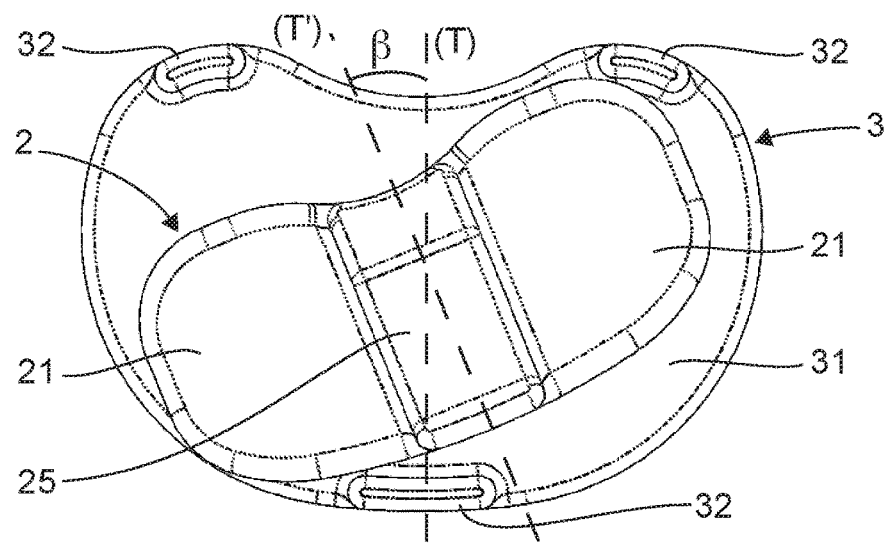
FIG. 5A is a top view of the tibial plateau and of the mobile plate when the transversal axis of the mobile plate and the transversal axis of the tibial plateau form an angle of +15°.
Figure 5B:
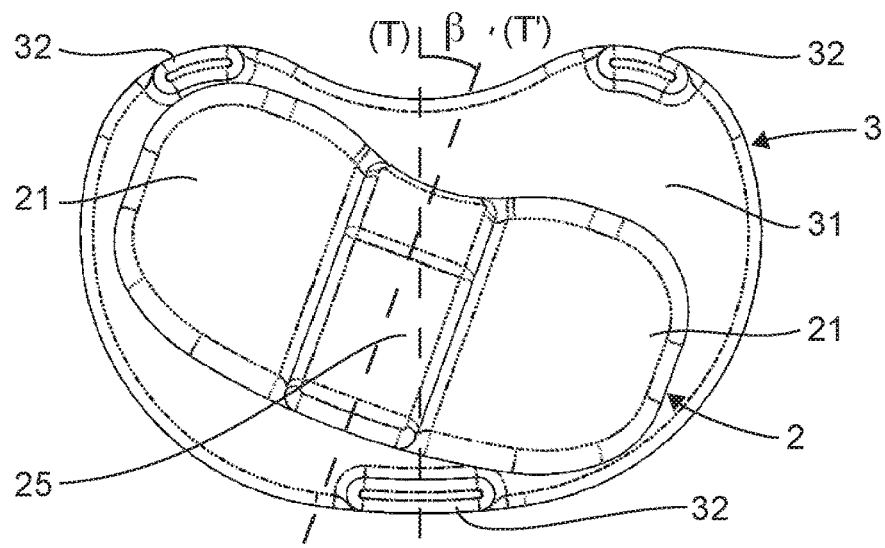
FIG. 5B is a top view of the tibial plateau and of the mobile plate when the transversal axis of the mobile plate and the transversal axis of the tibial plateau form an angle of −15°.
Figure 5C:
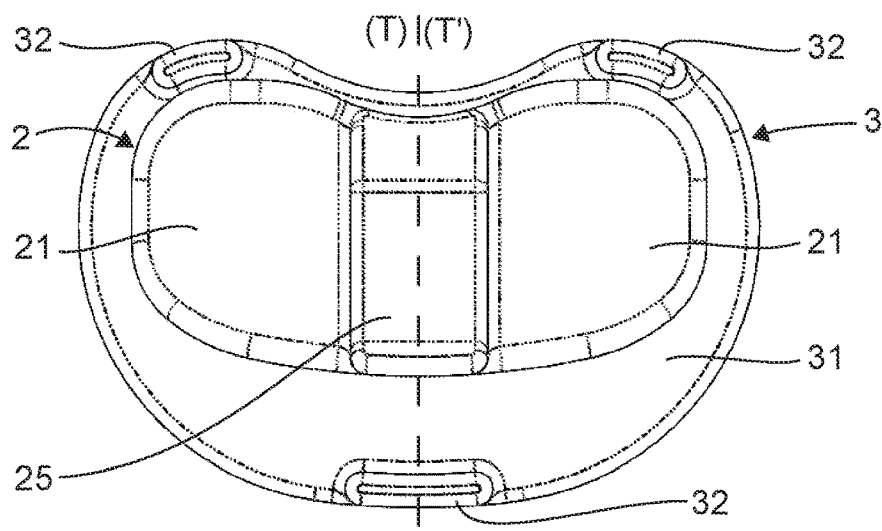
FIG. 5C is a top view of the tibial plateau and of the mobile plate when the transversal axis of the mobile plate and the transversal axis of the tibial plateau form a zero (0°) angle.

In the same way, FIGS. 5A to 5C present a top view of the relative movement of the mobile plate 2 on the tibial plateau 3. As can be noted, the perimeter of the plate 2 is smaller than that of the plateau 3 so that the mobile plate 2 can shift on the surface of the plateau 3. The three stops 32 define a perimeter or field of movement of the mobile plate 2. These top views are intended to illustrate the amplitude of the permitted movement of the mobile plate relative to the tibial plateau.

As can be seen in FIGS. 5A and 5B, the plate 2 can pivot about its longitudinal axis, parallel to that of the tibial plateau (not shown in the figures). More specifically, the transversal axis of the tibial plateau 2 can form an angle β of about 15° relative to the transversal axis T' of the mobile plate 2.

By convention, an angle is denoted as being an angle of +15° when the rotation is made in the clockwise sense (FIG. 5B) and −15° when the rotation is made in the anticlockwise sense (FIG. 5C).

7. VARIANTS

Different variants of the invention can be envisaged. For example the condyles and condylar bowls can both have the shape of cylinder portions while the intercondylar gap and the intercondylar stud take the form of a sphere portion. Conversely, the condyles and condylar bowls can both take the shape of a sphere portion while the intercondylar gap and intercondylar stud take the shape of a cylinder portion. It is also possible for one condyle and its corresponding condylar bowl to take the shape of a sphere portion while the other will take the shape of a cylinder portion.

In another variant, compatible with the variants listed here above, the tibial plateau is devoid of stops. In this case, the leg of the patient being operated on is held still by a splint while fibrous tissue is formed about the prosthesis to stabilize the replaced joint.

An exemplary embodiment of the present disclosure overcomes the drawbacks of the prior art.

An exemplary embodiment provides a knee prosthesis that is more resistant than presently used prostheses.

An exemplary embodiment implements a prosthesis of this kind that allows patients to resume normal physical activity.

An exemplary embodiment proposes a prosthesis that limits inflammatory reactions.

An exemplary embodiment proposes a prosthesis that enables the re-forming of a fibrous tissue that is more resistant, and plays the natural role of the knee ligaments by remodeling fibrous structures under mechanical stress.

An exemplary embodiment proposes a prosthesis, the joint or articular surfaces (the surfaces of mutual friction) of which have improved congruency in a load-bearing area.

An exemplary embodiment proposes a prosthesis that enables greater amplitude of motion as compared with known knee prostheses.

The invention claimed is:

1. A total knee prosthesis to be implanted in a human patient, said prosthesis comprising:
   a femoral element having a longitudinal axis;
   a tibial plateau having a longitudinal axis-; and
   a mobile plate, said mobile plate being interposed between the femoral element and the tibial plateau to form two joints with them wherein:
   a. said femoral element, mobile plate and tibial plateau are each formed by a distinct part and entirely constituted out of one and the same ceramic material, and said fermoral element, mobile plate and tibial plateau do not include any alloy with plastic material or metal material, and do not have any holes or perforations;
   b. the surfaces of mutual friction of the femoral element with the mobile plate and the surfaces of mutual friction of the tibial plateau with the mobile plate are entirely constituted by said one and the same ceramic material; and
   c. the mobile plate comprises two condylar bowls, and the femoral element comprises two condyles, said condyles and said condylar bowls each comprising surfaces of mutual friction spaced apart from each other by a distance smaller than 100 μm when the longitudinal axes of said femoral element and said tibial plateau form an angle of 0° to 75°, and
   wherein said mobile plate comprises an intercondylar stud forming a projection toward said femoral element, said intercondylar stud being monolithically formed with the condylar bowls and having an upper surface and two lateral surfaces,
   wherein said femoral element comprises an intercondylar gap forming a rail that houses said intercondylar stud, said intercondylar gap having two parallel lateral surfaces,
   wherein the upper surface of the intercondylar stud corresponds to the shape of the intercondylar gap and the two lateral surfaces of the intercondylar stud correspond to the ones of the parallel lateral surfaces of the intercondylar gap, forming three surfaces of mutual friction,
   wherein the tibial plateau has an upper surface cooperating with a lower surface of the mobile plate forming the surface of mutual friction between said mobile plate and said tibial plateau, said upper surface of the tibial plateau and said lower surface of the mobile plate being essentially planar, entire and uninterrupted.

2. The total knee prosthesis according to claim 1, wherein said condylar bowls and said condyles are spaced apart from one another by a distance of less than 100 μm when the longitudinal axes of said femoral element and of said tibial plateau form an angle of 0° to 60°.

3. The total knee prosthesis according to claim 1, wherein the femoral element and the tibial plateau are mobile in rotation relative to each other on an angular range of flexion of 0° to 135°.

4. The total knee prosthesis according to claim 1, wherein the surfaces of mutual friction of the condyles and of the condylar bowls are cylinder portions generated by revolution having a same radius.

5. The total knee prosthesis according to claim 1, wherein said mobile plate has a perimeter smaller than the perimeter of an upper surface of the tibial plateau.

6. The total knee prosthesis according to claim 1, wherein said tibial plateau comprises at least three stops forming a projection towards said mobile plate, said stops making it possible to limit movements of the mobile plate on the surface of the tibial plateau.

7. The total knee prosthesis according to claim 1, wherein said mobile plate can pivot on said tibial plateau such that a transversal axis of the mobile plate forms an angle up to +15° relative to a transversal axis of the tibial plateau when movement takes place in a clockwise sense and such that the transversal axis of the mobile plate forms an angle of up to −15° relative to the transversal axis of the tibial plateau when movement takes place in an anticlockwise sense.

8. The total knee prosthesis according to claim 1, wherein a space between the surfaces of mutual friction of the mobile plate and of the tibial plateau is smaller than 100 μm.

9. The total knee prosthesis according to claim 1, wherein said ceramic material has a thickness of 4 mm to 14 mm.

10. The total knee prosthesis according to claim 1, wherein said ceramic material is alumina $Al_2O_3$.

* * * * *